US009693803B2

United States Patent
Mamiya (10) Patent No.: US 9,693,803 B2
(45) Date of Patent: Jul. 4, 2017

(54) PUNCTURE NEEDLE FOR ENDOSCOPE AND BIOPSY SYSTEM

(71) Applicant: OLYMPUS CORPORATION, Hachioji-shi, Tokyo (JP)

(72) Inventor: Tomohiko Mamiya, Kawasaki (JP)

(73) Assignee: OLYMPUS CORPORATION, Tokyo (JP)

( * ) Notice: Subject to any disclaimer, the term of this patent is extended or adjusted under 35 U.S.C. 154(b) by 0 days.

(21) Appl. No.: 15/354,901

(22) Filed: Nov. 17, 2016

(65) Prior Publication Data

US 2017/0065296 A1    Mar. 9, 2017

Related U.S. Application Data

(63) Continuation of application No. PCT/JP2015/084281, filed on Dec. 7, 2015.

(30) Foreign Application Priority Data

Feb. 27, 2015    (JP) ................................ 2015-038207

(51) Int. Cl.
*A61B 17/34*    (2006.01)
*A61B 10/04*    (2006.01)
*A61B 1/00*    (2006.01)
*A61B 10/02*    (2006.01)

(52) U.S. Cl.
CPC ............ *A61B 17/3478* (2013.01); *A61B 1/00* (2013.01); *A61B 10/02* (2013.01); *A61B 10/04* (2013.01); *A61B 17/34* (2013.01); *A61B 2010/045* (2013.01)

(58) Field of Classification Search
CPC ............................ A61B 10/04; A61B 17/3478
See application file for complete search history.

(56) References Cited

FOREIGN PATENT DOCUMENTS

| JP | 2002-306497 A | | 10/2002 |
|---|---|---|---|
| JP | 2005-073798 A | | 3/2005 |
| JP | 2005-137815 A | | 6/2005 |
| JP | 2005-312828 A | | 11/2005 |
| JP | 2010-042139 A | | 2/2010 |
| JP | 2010042139 A | * | 2/2010 |
| JP | 2013-103061 A | | 5/2013 |

OTHER PUBLICATIONS

Feb. 9, 2016 International Search Report issued in International Patent Application No. PCT/JP2015/084281.

* cited by examiner

*Primary Examiner* — Michael C Stout
*Assistant Examiner* — Nicholas E Kolderman
(74) *Attorney, Agent, or Firm* — Oliff PLC (57) ABSTRACT

A puncture needle for an endoscope includes a flexible sheath having a longitudinal axis and deformed to be bent by a raising base, a flexible needle tube having a needle tip and a distal opening section and that is movable in the sheath with respect to the sheath, and a stylet having a distal end surface that is able to advance and retreat in the needle tube and protrude and withdraw from needle tube along the longitudinal axis of the sheath, wherein the stylet retracts the needle tip such that the needle tip of the needle tube is separated from an inner surface of the sheath as the distal end surface of the stylet comes in contact with the inner surface of the sheath formed in the bent shape.

7 Claims, 11 Drawing Sheets

PUNCTURE NEEDLE FOR ENDOSCOPE AND BIOPSY SYSTEM

This application is a continuation application, based on PCT/JP2015/084281, filed on Dec. 7, 2015, claiming priority based on Japanese Patent Application No. 2015-038207, filed in Japan on Feb. 27, 2015, the content of which is incorporated herein by reference.

FIELD OF THE INVENTION

The present invention relates to a puncture needle for an endoscope and a biopsy system.

DESCRIPTION OF THE RELATED ART

In the related art, an inspection method that is referred to as a biopsy of collecting a small amount of body tissue and observing the body tissue using a microscope is known. When tissue of a deep part of an organ or the like is collected, since observation by an optical endoscope becomes difficult, an ultrasonogram of the organ is acquired by an ultrasonic endoscope or the like, and a biopsy needle is inserted in the organ to collect the tissue under ultrasonic observation.

For example, Japanese Unexamined Patent Application, First Publication No. 2005-312828 discloses a puncture needle including a needle tube inserted in a sheath, and having a configuration that the needle tube is inserted into the tissue.

In addition, Japanese Unexamined Patent Application, First Publication No. 2005-073798 discloses a puncture needle apparatus for an endoscope having a tubular puncture needle inserted into a sheath, and a blade surface having an inclined surface shape sharpened toward a distal end thereof is formed at at least one of an outer circumferential surface and an inner circumferential surface of a distal portion of the puncture needle.

SUMMARY OF THE INVENTION

Means for Solving the Problem

An aspect of the present invention is a puncture needle that is used with an endoscope having a channel through which a medical instrument is inserted and a bending section configured to bend the medical instrument in the channel, the puncture needle being configured to be inserted through the channel as the medical instrument, the puncture needle comprising: a flexible sheath having a longitudinal axis and deformed to be bent by the bending section; a flexible needle tube having a needle tip section and an opening section formed in the needle tip section, and movable in the sheath with respect to the sheath; a stylet having a distal end surface that is configured to advance and retreat in the needle tube along the longitudinal axis of the sheath, and to protrude from and retract into the needle tube, and that is configured to be positioned with respect to the needle tube in a state in which the distal end surface of the stylet protrudes from the opening section of the needle tube; a manipulation section attached to the sheath and configured to advance and retract the needle tube with respect to the sheath; and a positioning mechanism installed at the manipulation section and configured to hold the stylet with respect to the needle tube at a position at which the distal end surface of the stylet protrudes from the opening section of the needle tube, wherein, in a state in which the puncture needle for an endoscope is disposed in the channel, when the distal end surface of the stylet is pressed from an inner surface of the sheath bent by the bending section, a needle tip of the needle tube is moved away from an inner surface of the sheath in a state in which the distal end surface of the stylet is positioned by the positioning mechanism with respect to the needle tube.

In a state in which a bending radius of curvature of a bent shape in the bending section which bends the sheath is minimum, a length from the opening section of the needle tube to the distal end surface of the stylet may be maintained in a positional relation in which the distal end surface of the stylet comes in contact with an inner circumferential surface of the sheath and the needle tip is spaced from the inner circumferential surface of the sheath.

The needle tube may have: a principal inclined surface having a flat surface shape inclined with respect to a centerline of the needle tube; and a back-cut processed surface inclined with respect to the centerline of the needle tube and having a flat surface shape crossing the principal inclined surface to form the needle tip on an intersection line with the principal inclined surface.

The needle tube may have a curved blade surface configured to form a part of a conical surface about a straight line coaxial with or parallel to the centerline of the needle tube when the needle tube is in a straight state and configuring the needle tip on a boundary line with the inner circumferential surface of the needle tube.

The sheath may have: a coil body formed of a metal wire wound in a coil shape and having an inner diameter larger than an outer diameter of the needle tube; and a resin tube disposed in the coil body and coaxial with the coil body and having an inner diameter larger than the outer diameter of the needle tube.

Another aspect of the present invention is a biopsy system including an endoscope having a channel through which a medical instrument is inserted and a bending section configured to bend the medical instrument in the channel; and the puncture needle for an endoscope according to the above-mentioned aspect.

The bending section may have at least any one of: a bendable section configured to bend the channel, and a raising base configured to press an outer surface of the sheath to define a protrusion direction of the medical instrument from a distal end of the channel, and wherein a protrusion distance from an opening section of the needle tube of the puncture needle to the distal end surface of the stylet is defined based on the smaller one of the minimum radius of curvature of the sheath by the bendable section and the minimum radius of curvature of the sheath by the raising base.

DETAILED DESCRIPTION OF THE INVENTION

First Embodiment

Figure 1:
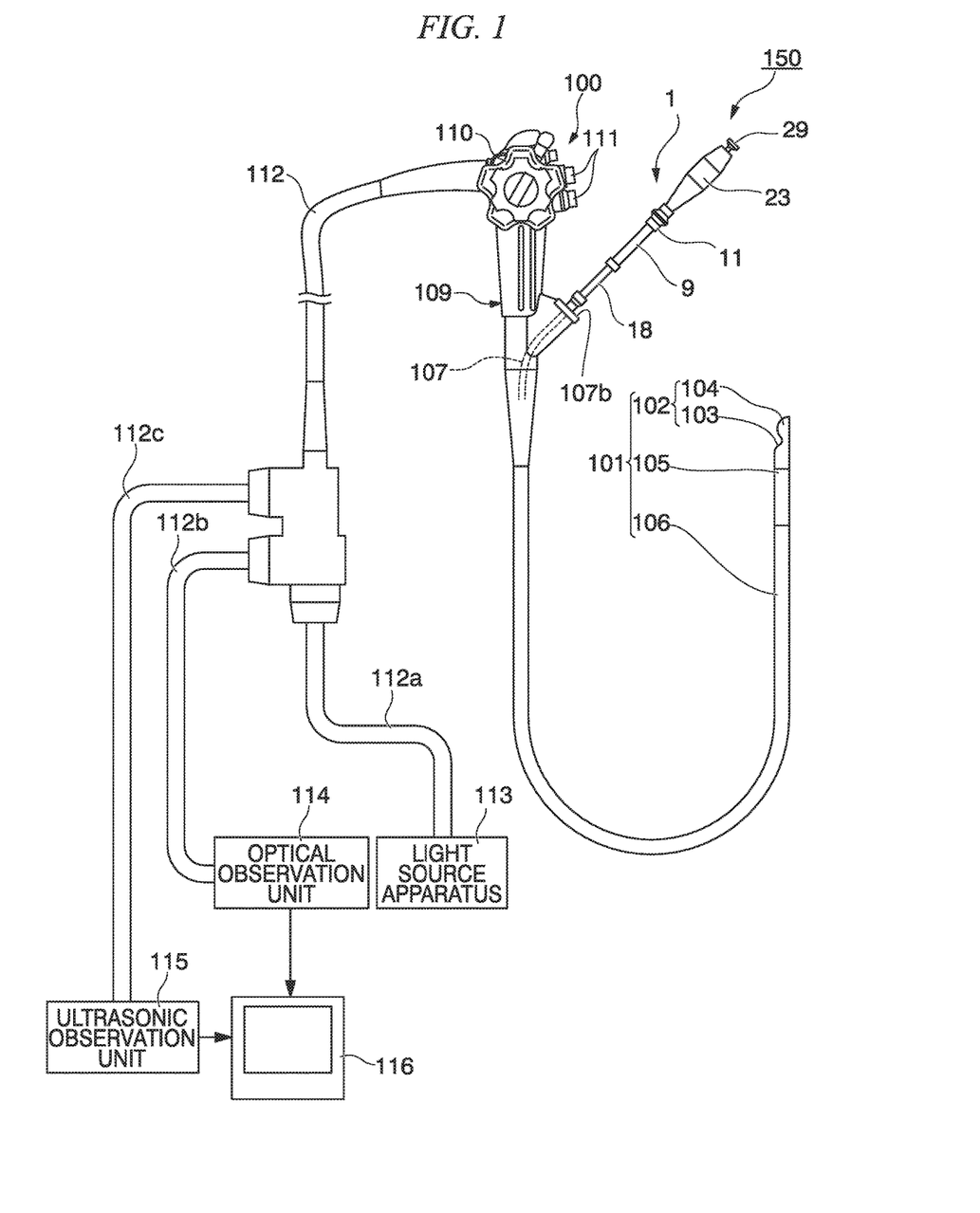
FIG. 1 is a view showing a schematic configuration of a puncture needle for an endoscope of a first embodiment of the present invention and a biopsy system of the embodiment including an ultrasonic endoscope.
Figure 2:
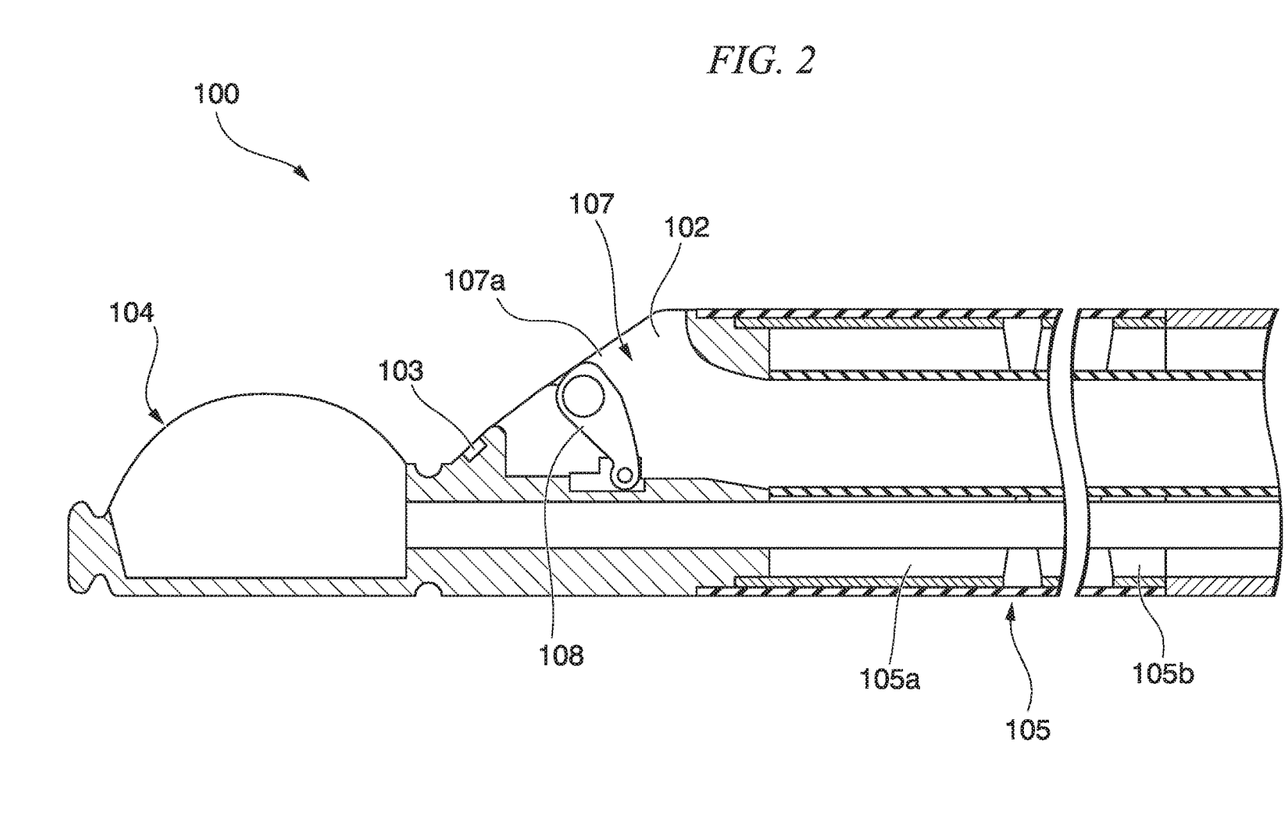
FIG. 2 is a cross-sectional view of a distal portion of the ultrasonic endoscope serving as an endoscope of the biopsy system.

A first embodiment of the present invention will be described. FIG. 1 is a view showing a schematic configuration of a puncture needle for an endoscope of the embodiment and a biopsy system of the embodiment including an ultrasonic endoscope. FIG. 2 is a cross-sectional view of a distal portion of the ultrasonic endoscope serving as an endoscope of the biopsy system.

A puncture needle 1 for an endoscope (hereinafter, simply referred to as "the puncture needle 1") of the embodiment shown in FIG. 1 is a part of a biopsy system 150, and is a biopsy needle for use in a biopsy combined with an ultrasonic endoscope 100.

First, an example of an endoscope used with the puncture needle 1 of the embodiment will be described. Further, a configuration of the endoscope that can be used with the puncture needle 1 of the embodiment is not particularly limited.

The ultrasonic endoscope 100 exemplified in the embodiment is an endoscope that can be applied to perform diagnosis or treatment on digestive organs or respiratory organs. The ultrasonic endoscope 100 includes an insertion section 101 configured to be inserted into a body from a distal end thereof, an operation section 109 attached to a proximal end of the insertion section 101, a universal cord 112 having a first end connected to a side portion of the operation section 109, a light source apparatus 113 connected to a second end of the universal cord 112 via a branch cable 112a, an optical observation unit 114 connected to the second end of the universal cord 112 via a branch cable 112b, and an ultrasonic observation unit 115 connected to the second end of the universal cord 112 via a branch cable 112c.

The insertion section 101 has a distal hard section 102, a bendable section 105 and a flexible tube section 106 in sequence from a distal side.

As shown in FIGS. 1 and 2, the distal hard section 102 includes an optical imaging mechanism 103 configured to perform optical observation, an ultrasonic scanning mechanism 104 configured to perform ultrasonic observation, and a raising base 108 configured to adjust a direction of the puncture needle 1 inserted into a channel 107, which will be described below.

The optical imaging mechanism 103 includes an observation optical system in which a field of vision is directed toward an inclined forward side of the distal hard section 102, an image sensor such as a CCD, a CMOS, or the like, configured to detect an image of a subject that enters through the observation optical system, and various configurations (not shown) such as a CPU or the like configured to control an operation of the image sensor.

The ultrasonic scanning mechanism (a probe) 104 includes an ultrasonic vibrator (not shown) configured to emit and receive ultrasonic waves. The ultrasonic scanning mechanism 104 receives the reflected waves obtained when the ultrasonic waves emitted from the ultrasonic vibrator hit the observation target and are reflected using the ultrasonic vibrator, and outputs a signal to the ultrasonic observation unit 115 based on the ultrasonic waves received by the ultrasonic vibrator. The ultrasonic scanning mechanism 104 of the embodiment is used to acquire an ultrasonic wave image of the tissue serving as a biopsy target or acquire an ultrasonic wave image of a needle tube 3 in a process of a procedure of the biopsy.

The bendable section 105 is formed in a tubular shape. When a pulling operation of an angle wire (not shown) fixed to a distal end 105a (see FIG. 2) of the bendable section 105, which is located more proximal to the ultrasonic scanning mechanism 104 than a proximal end 105b of the bendable section 105, and extending to the operation section 109 is performed in the operation section 109, the bendable section 105 can be bent in a predetermined direction. The bendable section 105 of the embodiment can be bent in directions that follow a scanning direction of the ultrasonic waves and directions perpendicular to the scanning direction.

Further, the ultrasonic endoscope 100 of the embodiment may have a bendable section having a small outer diameter of an insertion section and bendable only in two directions following the scanning direction of the ultrasonic waves in order to perform treatment of, for example, the respiratory organs.

The flexible tube section 106 is a tubular member flexibly formed such that the distal hard section 102 in hollow organ or a body cavity can be guided to a desired position.

The channel 107 and a duct (not shown) configured to perform supply of air and supply of water, suction, or the like, are formed in the bendable section 105 and the flexible tube section 106, respectively.

The channel 107 shown in FIGS. 1 and 2 is a tubular portion configured to allow insertion of the puncture needle 1 of the embodiment and the other known medical instruments. A first end (a distal end opening 107a) of the channel 107 is opened in the vicinity of a distal portion of the distal hard section 102. A second end of the channel 107 is opened at a side surface of a distal portion of the operation section 109. A proximal port member 107b formed in a flange shape is fixed to the second end of the channel 107. The puncture needle 1 used with the ultrasonic endoscope 100 can be fixed to the proximal port member 107b. In the embodiment, the raising base 108 is disposed at a distal end of the channel 107.

The raising base 108 is a member configured to vary an orientation of a distal portion of a sheath 7 of the puncture needle 1 to a direction crossing a centerline of the insertion section 101. The raising base 108 can press an outer surface of the sheath 7 to deform the sheath 7 in a bent state by pulling a raising wire (not shown) extending to the operation section 109 in the operation section 109. The raising base 108 of the embodiment is a bending section configured to bend the sheath 7 in a state in which the sheath 7 is disposed at the raising base 108.

Further, the ultrasonic endoscope 100 may include a slope formed at the distal hard section 102 and configured to restrict a protrusion direction of the puncture needle 1 to a predetermined direction, instead of the raising base 108. The slope in this case is also an example of the bending section configured to come in contact with the outer surface of the sheath 7 to bend the sheath 7.

The operation section 109 shown in FIG. 1 includes a bending operation mechanism 110 having an outer surface formed such that an operator who uses the ultrasonic endoscope 100 can hold the mechanism with her or his hands and configured to operate the bendable section 105 and the raising base 108, and a plurality of switches 111 configured to perform supply of air, supply of water or suction through the duct.

The light source apparatus 113 is an apparatus for emitting illumination light to perform imaging using the optical imaging mechanism 103.

The optical observation unit 114 is configured to project a picture imaged by an image sensor of the optical imaging mechanism 103 on a monitor 116.

The ultrasonic observation unit 115 is configured to receive a signal output from the ultrasonic scanning mechanism 104, and generate an image based on the signal to project the image on the monitor 116.

Figure 3:
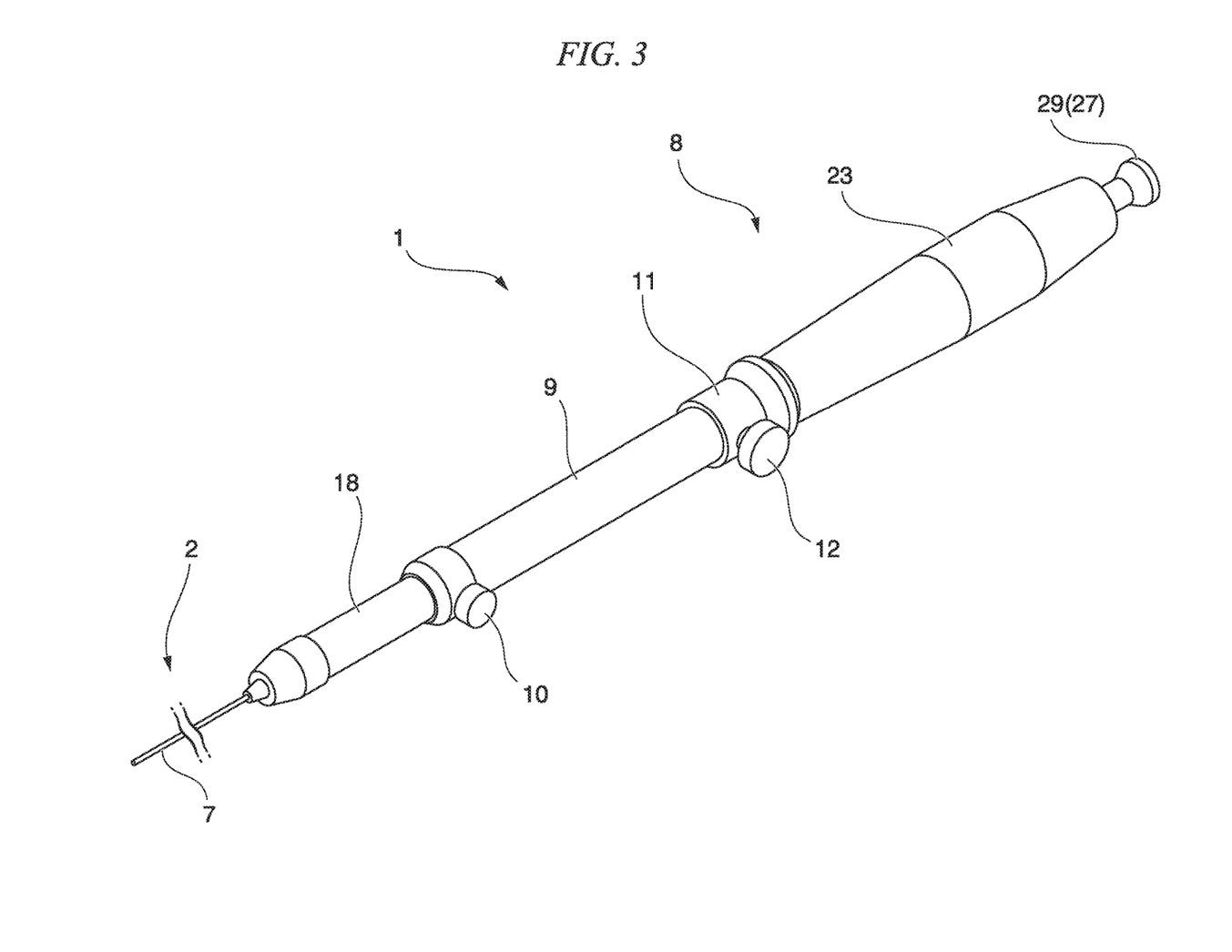
FIG. 3 is a perspective view of the puncture needle for an endoscope.
Figure 4:
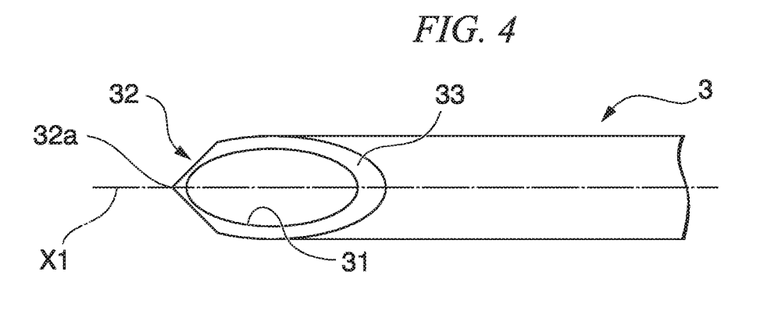
FIG. 4 is a plan view showing a distal portion of a needle tube of the puncture needle for an endoscope.
Figure 5:
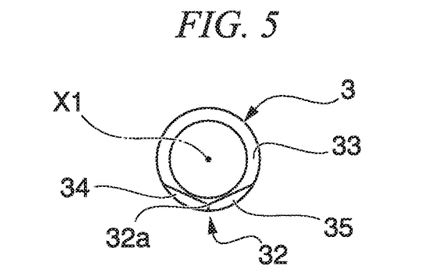
FIG. 5 is a front view showing the distal portion of the needle tube.
Figure 6:
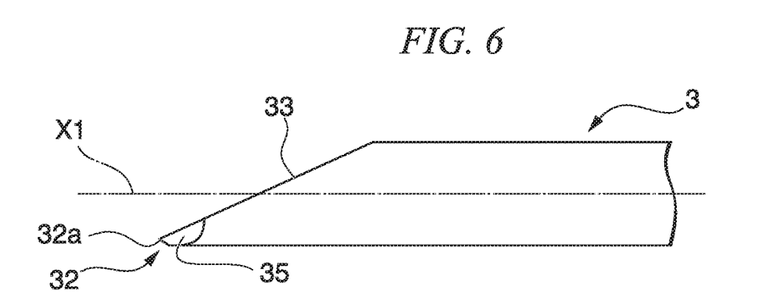
FIG. 6 is a side view showing the distal portion of the needle tube.
Figure 7:
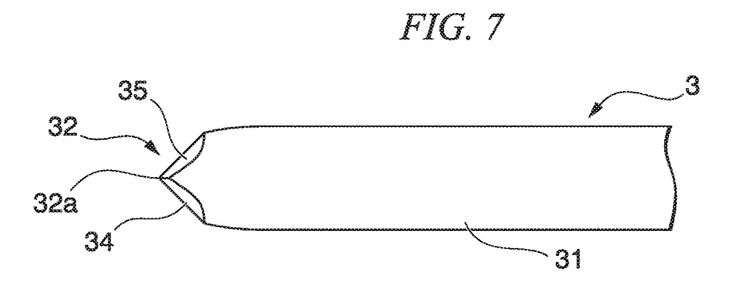
FIG. 7 is a bottom view showing the distal portion of the needle tube.

Next, a configuration of the puncture needle 1 will be described. FIG. 3 is a perspective view of the puncture needle for an endoscope. FIG. 4 is a plan view showing a distal portion of the needle tube of the puncture needle for an endoscope. FIG. 5 is a front view showing the distal portion of the needle tube. FIG. 6 is a side view of the distal portion of the needle tube. FIG. 7 is a bottom view showing the distal portion of the needle tube.

The puncture needle 1 includes an insertion body 2 configured to be inserted into a body, a manipulation section (a treatment tool manipulation section) 8 configured to operate the insertion body 2, and a stylet 27.

The insertion body 2 is an elongated member that can be attached to the channel 107 to protrude from the distal end of the insertion section 101 of the ultrasonic endoscope 100 shown in FIGS. 1 and 2. The insertion body 2 includes the needle tube 3 (see FIG. 4) and the tubular sheath 7 through which the needle tube 3 is inserted.

As shown in FIGS. 4 to 7, the needle tube 3 is a flexible tubular member having a needle tip section 32 being formed with a distal opening section 31 and a needle tip 32a, a principal inclined surface 33, and back-cut processed surfaces 34 and 35. The needle tube 3 is operated to advance and retreat in the sheath 7 by the manipulation section 8. The distal end of the needle tube 3 can protrude and retract from the opening of the distal portion of the sheath 7.

The needle tube 3 is an elastic tubular member having flexibility and configured to easily recover the tubular member to a linear state even when the tubular member is bent by an external force. For example, an alloy material such as a stainless alloy, a nickel titanium alloy, a cobalt chrome alloy, or the like, may be employed as a material of the needle tube 3.

The distal opening section 31 of the needle tube 3 is an opening defined by a boundary between the principal inclined surface 33 and the inner circumferential surface of the needle tube 3 as an edge, and has an elliptical shape that is inclined with respect to a centerline X1 of the needle tube 3 thereof.

The needle tip 32a is the most distal end of the needle tube 3 and is sharpened to be inserted into the tissue.

The principal inclined surface 33 is formed in a flat surface shape that is inclined with respect to the centerline X1 of the needle tube 3. An inclination angle of the principal inclined surface 33 with respect to the centerline X1 of the needle tube 3 may be appropriately set in consideration of the puncture performance with respect to the tissue.

The back-cut processed surfaces 34 and 35 are formed in a flat surface shape crossing the principal inclined surface 33 while inclined with respect to the centerline X1 of the needle tube 3. As the needle tip 32a is configured on a line of intersection between the back-cut processed surfaces 34 and 35 and the principal inclined surface 33, in the embodiment, the needle tip 32a has a point shape.

The back-cut processed surfaces 34 and 35 formed at the outer circumferential surface of the needle tip section 32 of the needle tube 3 are inclined in a direction substantially opposite to the inclination direction of the distal opening section 31.

Figure 8:
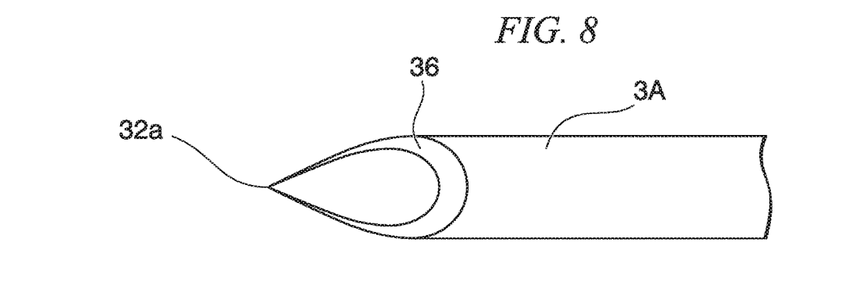
FIG. 8 is a plan view showing another configuration of the distal portion of the needle tube of the puncture needle for an endoscope.
Figure 9:
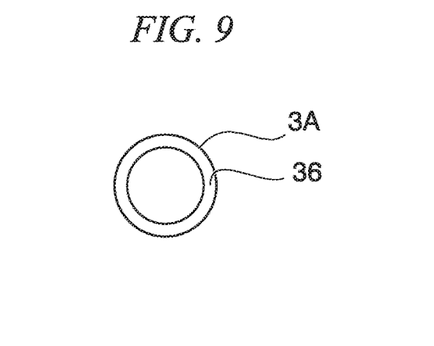
FIG. 9 is a front view showing the distal portion of the needle tube.
Figure 10:
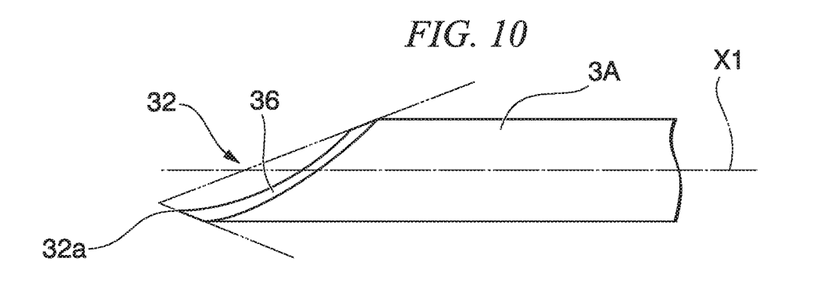
FIG. 10 is a side view showing the distal portion of the needle tube.
Figure 11:
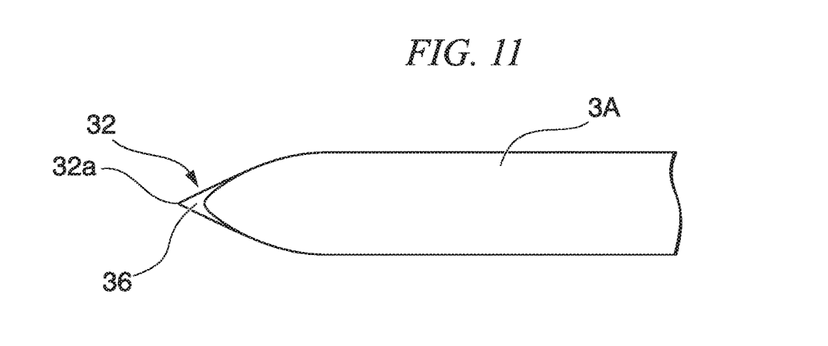
FIG. 11 is a bottom view showing the distal portion of the needle tube.

Further, the configuration of the needle tube 3 is not limited to the above-mentioned configuration. FIGS. 8 to 11 show another configuration example of the needle tube 3. FIG. 8 is a plan view showing another configuration example of the distal portion of the needle tube of the puncture needle for an endoscope. FIG. 9 is a front view showing the distal portion of the needle tube. FIG. 10 is a side view showing the distal portion of the needle tube. FIG. 11 is a bottom view showing the distal portion of the needle tube.

As shown in FIGS. 8 to 11, for example, instead of the above-mentioned needle tube 3, the puncture needle 1 of the embodiment may have a needle tube 3A having a curved blade surface 36 that is formed of a portion of a conical surface. The needle tip 32a of the needle tube 3A is disposed on a boundary line between the inner circumferential surface of the needle tube 3A and the blade surface 36. As a specific example, in the needle tube 3A, the blade surface 36 has a curved surface being formed in a shape of a part of a conical surface about the coaxial centerline as the centerline of the needle tube 3A or a straight line parallel to the centerline when the needle tube 3A is in a linear state.

The sheath 7 shown in FIG. 3 is a tubular member having a longitudinal axis and the needle tube 3 is inserted thereinto. The sheath 7 is formed of a resin, a metal, or the like. The distal end of the sheath 7 is opened such that the needle tube 3 can protrude. The proximal end of the sheath 7 is fixed to the distal portion of the manipulation section 8.

The manipulation section 8 includes a manipulation main body 9, an attachment adaptor 18 disposed at a distal side of the manipulation main body 9, and a needle slider 23 disposed at a proximal side of the manipulation main body 9.

The manipulation main body 9 is formed of, for example, ABS resin or the like, and has a lumen through which the needle tube 3 and the sheath 7 can be inserted. The attachment adaptor 18 formed in a tubular shape is inserted into the distal side of the manipulation main body 9. The proximal side of the manipulation main body 9 is inserted into the needle slider 23 formed in a tubular shape. The manipulation main body 9 and the attachment adaptor 18, and the manipulation main body 9 and the needle slider 23 can be slid in the axial direction while relative rotation about the axis is constrained by engaging of grooves, juts, or the like (not shown) formed on the outer circumferential surfaces. The sheath 7 disposed in the manipulation main body 9 is fixed to the manipulation main body 9.

The attachment adaptor 18 is a tubular member configured to fix the manipulation section 8 to the proximal port member 107*b* of the ultrasonic endoscope 100. The sheath 7, the needle tube 3 and the stylet 27 are inserted into the attachment adaptor 18. The attachment adaptor 18 is connected to the manipulation main body 9 to be coaxial with the manipulation main body 9. The attachment adaptor 18 and the manipulation main body 9 are fixed to each other by a fixing screw 10. When the fixing screw 10 is locked into the manipulation main body 9, the attachment adaptor 18 can be pushed against the manipulation main body 9 to fix the attachment adaptor 18 and the manipulation main body 9 without sliding therebetween. In addition, in a state in which the fixing screw 10 is loosened, the manipulation main body 9 can be moved with respect to the attachment adaptor 18 along a center axis of the attachment adaptor 18. The attachment adaptor 18 is configured such that the sheath 7 advances together with the needle tube 3 when the manipulation main body 9 is moved toward the distal side of the attachment adaptor 18 with respect to the attachment adaptor 18. Accordingly, when a positional relation between the attachment adaptor 18 and the manipulation main body 9 is varied, a protrusion length of the sheath 7 from the channel 107 when the manipulation section 8 is fixed to the ultrasonic endoscope 100 can be adjusted, and the protrusion length can be fixed by the fixing screw 10.

A concavo-convex portion may be formed at an outer circumferential surface of the distal portion of the attachment adaptor 18 such that an operator can easily grip the attachment adaptor 18.

Figure 12:
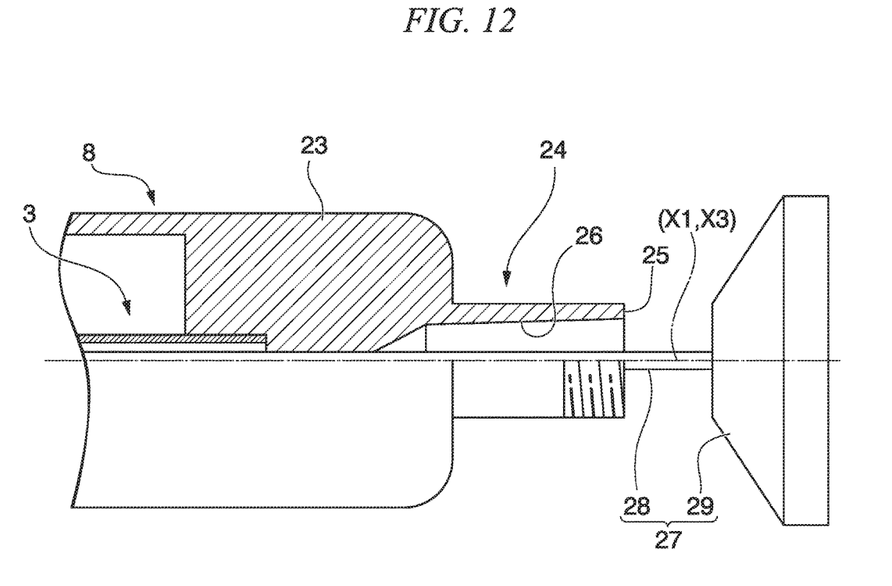
FIG. 12 is a cross-sectional view showing a proximal portion of a manipulation section of the puncture needle for an endoscope.

FIG. 12 is a cross-sectional view showing a proximal portion of the manipulation section 8 of the puncture needle 1 for an endoscope.

As shown in FIG. 12, the needle slider 23 is a tubular member configured to hold the proximal portion of the needle tube 3. That is, the proximal side of the needle tube 3 protrudes from the proximal end of the sheath 7 to extend to the inside of the needle slider 23, and is fixed to the needle slider 23 at the proximal portion of the needle slider 23. The needle slider 23 is connected to the manipulation main body 9 to be movable with respect to the manipulation main body 9. That is, the needle slider 23 is configured such that the needle tube 3 advance with respect to the sheath 7 when the needle slider 23 is moved toward the distal side of the manipulation main body 9 with respect to the manipulation main body 9.

A concavo-convex portion may be formed at the outer circumferential surface of the distal portion of the needle slider 23 such that an operator can easily grip the needle slider 23.

As shown in FIG. 3, a stopper 11 is movably attached to the manipulation main body 9 at the distal side of the needle slider 23. The stopper 11 has a fixing screw 12, and can be fixed to the manipulation main body 9 by fastening the fixing screw 12 thereinto. Since the needle slider 23 is restrained to be able to advance toward a position in contact with the stopper 11 with respect to the manipulation main body 9, the maximum protrusion length of the needle tube 3 from the sheath 7 can be adjusted by adjusting the fixing position of the stopper 11 with respect to the manipulation main body 9.

It is an initial state before the beginning of the use of the puncture needle 1 that the needle slider 23 is in the state of being disposed at which the needle slider 23 is moved to the proximal end of the manipulation main body 9. In the initial state, the distal end of the needle tube 3 is disposed in the sheath 7.

As shown in FIG. 12, a positioning mechanism 24 having an opening through which the stylet 27 is inserted into the needle tube 3 is formed at the proximal portion of the needle slider 23.

Figure 13:
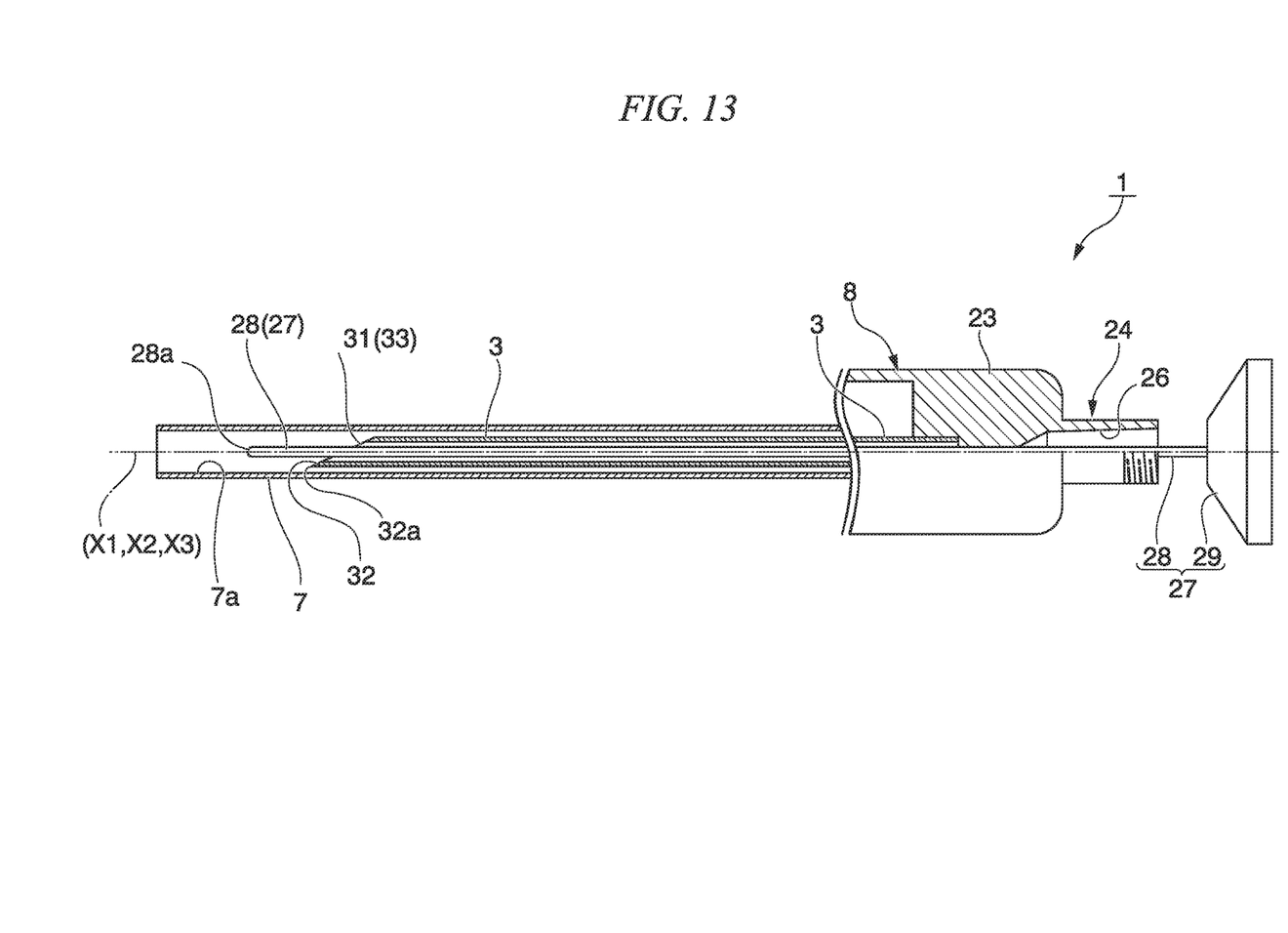
FIG. 13 is a partial cross-sectional view showing a positional relation between the needle tube and a stylet in a state in which the stylet is attached to the manipulation section.

FIG. 13 is a partial cross-sectional view for describing a positional relation between the needle tube and the stylet in a state in which the stylet is attached to the manipulation section.

As shown in FIGS. 12 and 13, the positioning mechanism 24 has a proximal end surface 25 that is able to abut a knob 29 of the stylet 27, and a port 26 that is able to be connected to a syringe. The positioning mechanism 24 defines a protrusion amount of the stylet 27 such that the stylet 27 protrudes from the distal opening section 31 of the needle tube 3 by a predetermined length in a state in which the knob 29 abuts the proximal end surface 25.

As shown in FIG. 13, the stylet 27 has a cored bar 28 that is able to be inserted into the needle tube 3, and the knob 29 that is able to abut the proximal end surface 25 of the positioning mechanism 24.

The cored bar 28 of the stylet 27 has a distal end surface 28*a* having a shape that does not easily scratch the inner surface of the sheath 7 upon contact with the inner surface of the sheath 7. The distal end surface 28*a* formed at the cored bar 28 of the stylet 27 of the embodiment is not sharp. The distal end surface 28*a* formed at the cored bar 28 of the stylet 27 of the embodiment has a curved surface such as a hemispherical outer surface to be convex toward the distal side. In addition, even when the stylet 27 has a surface perpendicular to a centerline X3 of the cored bar 28 as a distal end surface, the stylet 27 cannot easily scratch the inner surface of the sheath 7 as long as the stylet 27 is formed without edge such that the distal end surface and the outer circumferential surface of the cored bar 28 are smoothly connected.

A length of the cored bar 28 of the stylet 27 is defined to always protrude from the distal opening section 31 of the needle tube 3 in a state in which the knob 29 abuts the proximal end surface 25 of the positioning mechanism 24. A protrusion amount of the cored bar 28 from the distal opening section 31 of the needle tube 3 is determined in consideration of how much the sheath 7 is bent by the ultrasonic endoscope 100.

Figure 14:
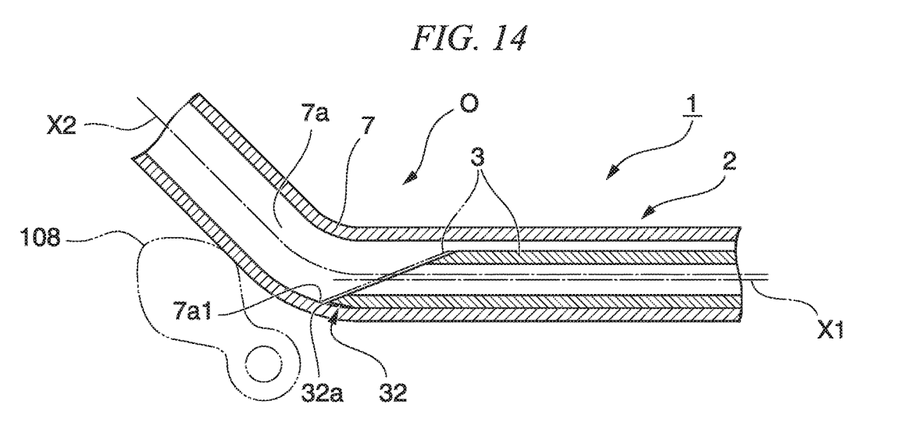
FIG. 14 is a schematic view showing an action in which a distal end surface of the stylet protrudes from a distal opening section of the needle tube.
Figure 15:
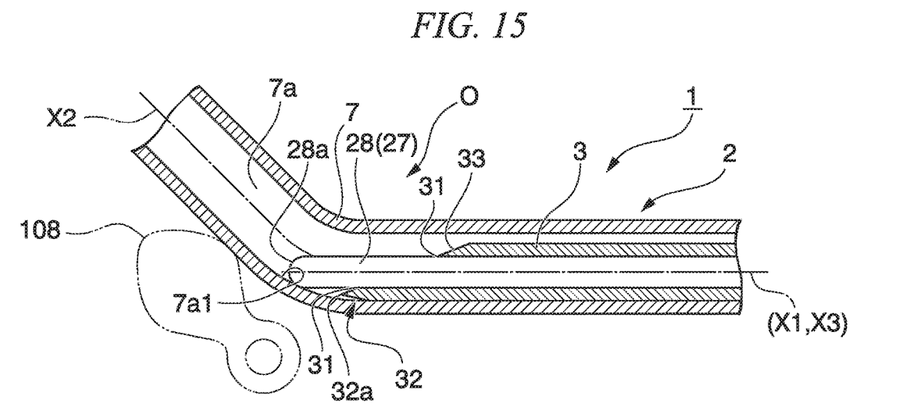
FIG. 15 is a schematic view showing an action in which the distal end surface of the stylet protrudes from the distal opening section of the needle tube.
Figure 16:
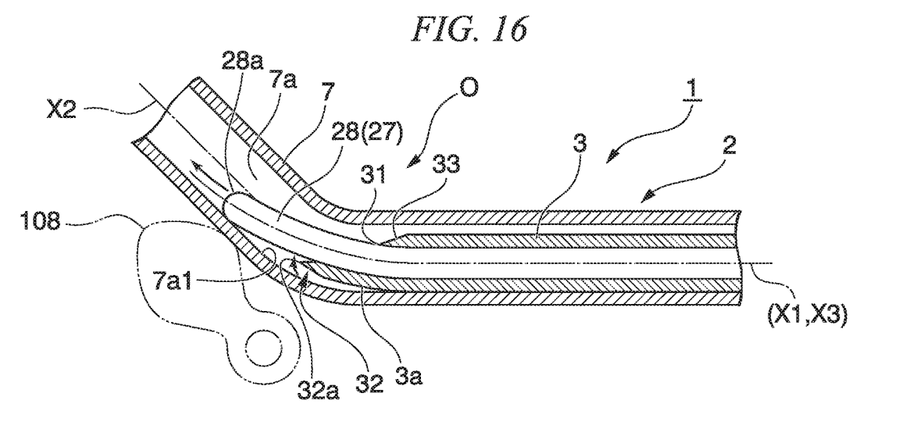
FIG. 16 is a schematic view showing an action in which the distal end surface of the stylet protrudes from the distal opening section of the needle tube.

FIGS. 14, 15 and 16 are schematic views for describing an action of the puncture needle 1 when the distal end surface of the stylet protrudes from the distal opening section of the needle tube.

For example, the ultrasonic endoscope 100 shown in FIGS. 1 and 2 bends the sheath 7 by pressing the outer surface of the sheath 7 using the bendable section 105 and the raising base 108. For example, the sheath 7 becomes bent as the outer surface of the sheath 7 is pressed by the raising base 108 as shown in FIG. 14. The sheath 7 in the bent state can be assumed to be bent along an arc having a certain center of curvature O. For this reason, when the distal portion (for example, the needle tip section 32) of the needle tube 3 comes in contact with an outer side portion 7a1 disposed at a distal position from a center of curvature in an inner circumferential surface 7a of the sheath 7 bent along the arc, the needle tube 3 may scratch the inner surface of the sheath 7.

For example, when the stylet 27 is not inserted into the needle tube 3 of the embodiment as shown in FIG. 14, the needle tip 32a of the needle tube 3 may stick in the outer side portion 7a1 of the sheath 7 formed in the bent shape along the arc as described above.

Here, as shown in FIGS. 15 and 16, when the cored bar 28 of the stylet 27 protrudes from the distal opening section 31 of the needle tube 3, the distal end surface 28a of the cored bar 28 and an outer circumferential surface 3a of the needle tube 3 come in contact with the outer side portion 7a1 of the sheath 7 formed in the bent shape along the arc. Further, the distal end surface 28a of the stylet 27 is pressed from the inner surface of the sheath 7, and the needle tip 32a of the needle tube 3 is withdrawn to a position separated from the outer side portion 7a1.

Since the needle tip 32a easily sticks in the inner surface of the sheath 7 in the case in which the sheath 7 is bent to have a smaller radius of curvature, in the embodiment, when the sheath 7 is deformed in a bent shape by the bendable section 105 and the raising base 108 in the ultrasonic endoscope 100 shown in FIGS. 1 and 2, a protrusion amount of the cored bar 28 from the distal opening section 31 is defined in consideration of a smaller one of a minimum radius of curvature of the sheath 7 by the bendable section 105 and a minimum radius of curvature of the sheath 7 by the raising base 108, i.e., a minimum radius of curvature corresponding to an upper limit of performance of the bending section of the ultrasonic endoscope 100. Accordingly, the needle tip 32a does not stick in the inner surface of the sheath 7 regardless of how the ultrasonic endoscope 100 serving as a target to which the puncture needle 1 is attached bends the sheath 7.

In the puncture needle 1 and the ultrasonic endoscope 100 of the embodiment, in a state in which a bending radius of curvature of the bending section (the bendable section 105 and the raising base 108) configured to bend the sheath 7 is minimum, a distance from the distal opening section 31 of the needle tube 3 to the distal end surface 28a of the stylet 27 is defined to have a positional relation in which the distal end surface 28a comes in contact with the inner circumferential surface of the sheath 7 and the needle tip 32a is separated from the inner circumferential surface of the sheath 7.

Incidentally, it is considered that the needle tip 32a cannot easily stick in the sheath 7 as long as an inclined state of the back-cut processed surfaces 34 and 35 formed at the needle tube 3 by back-cut processing is inclined adjacent to a surface perpendicular to the centerline X1 of the needle tube 3 (i.e., an angle formed between the back-cut processed surfaces 34 and 35 and the centerline X1 of the needle tube 3 is close to 90 degrees). However, making it difficult for the needle tip 32a to stick in the sheath 7 and making it easy for the needle tip 32a to be inserted in the tissue are at odds with each other. In the puncture needle 1 for biopsy, it is desirable that the tissue be easily pierced. In the embodiment, because the stylet 27 is used to make it difficult for the needle tip 32a to stick in the sheath 7, a shape for easily insertion into the tissue may be selected for the design of the needle tip 32a regardless of whether it easily sticks in the sheath 7.

Further, the extent to which the ultrasonic endoscope 100 bends the sheath 7 depends on a configuration or the like of the ultrasonic endoscope 100. For this reason, in the puncture needle 1 of the embodiment, configurations of the positioning mechanism 24 and the cored bar 28 are determined to correspond to the configuration of the ultrasonic endoscope under the assumption that the puncture needle 1 is used therewith.

Figure 17:
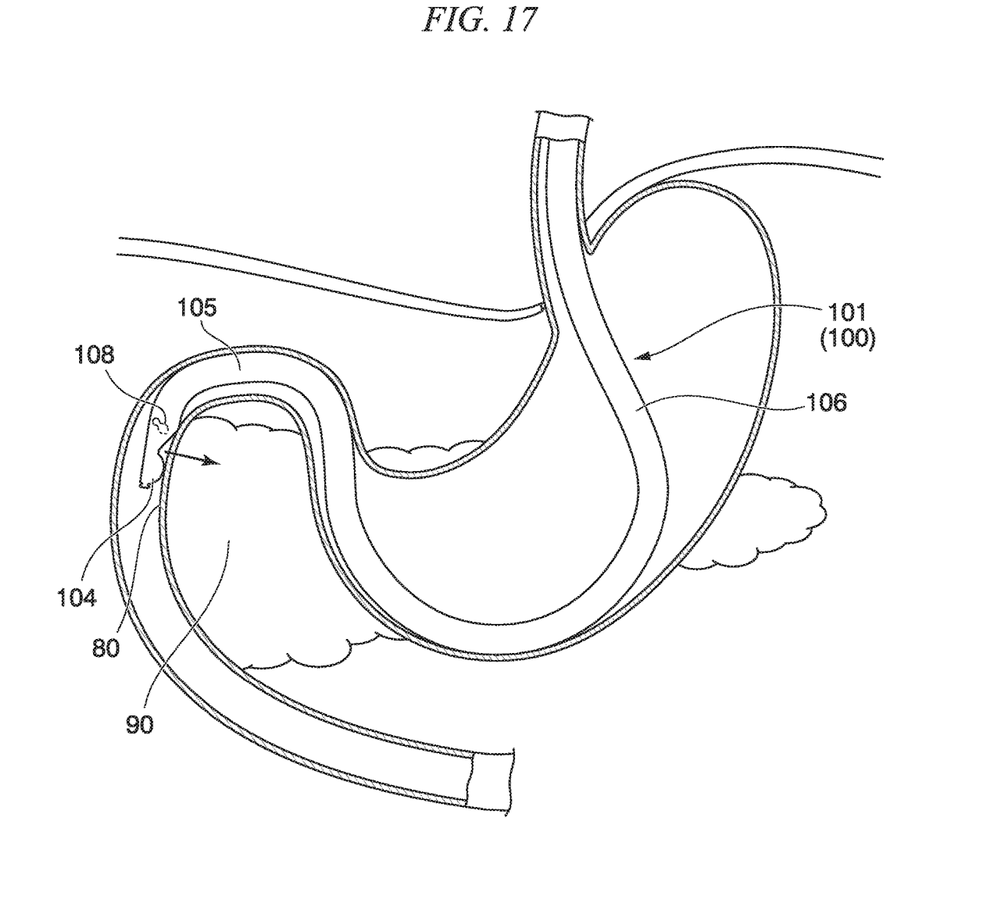
FIG. 17 is a schematic view showing a process of a procedure of a biopsy using the biopsy system.
Figure 18:
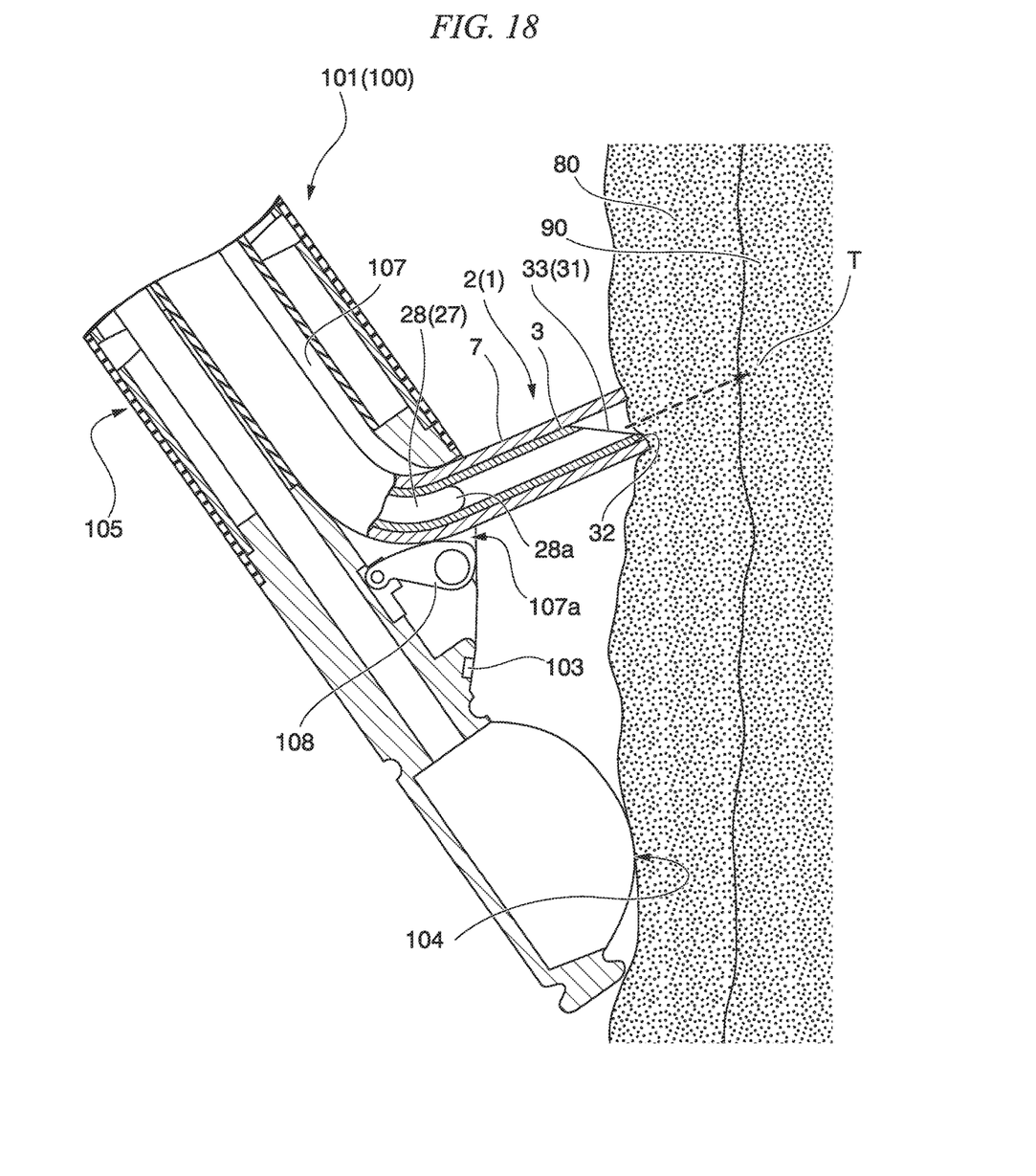
FIG. 18 is a schematic view showing a process just before puncture with the needle tube in the procedure.

An operation in use of the puncture needle 1 having the above-mentioned configuration will be described. FIG. 17 is a schematic view showing a process of a procedure of a biopsy using a biopsy system. FIG. 18 is a schematic view showing a process immediately before puncture with the needle tube in the procedure of the biopsy.

Hereinafter, an example of treatment of a biopsy of inserting the needle tube 3 of the puncture needle 1 into a lesion subjected to a target tissue in the body and collecting cells or the like of the lesion through the needle tube 3 will be described. The procedure of the biopsy shown in the embodiment is an example of a biopsy with respect to the head of pancreas in the pancreas 90 shown in FIGS. 17 and 18. Further, an application target of the puncture needle 1 of the embodiment is not limited to the head of pancreas.

First, an operator inserts the insertion section 101 of the ultrasonic endoscope 100 shown in FIG. 1 into the body, and introduces the distal portion of the insertion section 101 into the vicinity of the target tissue (in the embodiment, the head of pancreas) while appropriately bending the bendable section 105 under observation by the optical imaging mechanism 103. After introduction, the operator determines an area in which the biopsy is performed based on an observation result by the optical imaging mechanism 103 and the ultrasonic scanning mechanism 104. For example, when the biopsy with respect to the head of pancreas is performed, the insertion section 101 is moved in a state in which the bendable section 105 is bent such that the optical imaging mechanism 103 and the ultrasonic scanning mechanism 104 disposed at the insertion section 101 of the ultrasonic endoscope 100 arrive at the duodenum 80.

When the biopsy with respect to the head of pancreas is performed using the ultrasonic endoscope 100, in order to capture a puncture site of the puncture needle 1 in a field of vision of the ultrasonic endoscope 100, the bendable section 105 should be bent. In particular, when the biopsy with respect the head of pancreas is performed as in the embodiment, the bendable section 105 is bent to an extent close to a limit of performance of the bendable section 105 of the ultrasonic endoscope 100.

Next, the operator inserts the insertion body 2 of the puncture needle 1 from the distal side into the channel 107 from the proximal port member 107b formed at the manipulation section 109 of the ultrasonic endoscope 100 shown in FIG. 1. Further, the operator connects the attachment adaptor 18 of the manipulation section 8 to the proximal port member 107b. Accordingly, the manipulation section 8 of the puncture needle 1 is fixed to the ultrasonic endoscope 100 that is not rotated with respect to the operation section 109.

Next, the operator loosens the fixing screw 10 (see FIG. 3), relatively slides the attachment adaptor 18 and the manipulation main body 9 and adjusts a protrusion amount of the sheath 7 from the distal end of the insertion section 101 of the ultrasonic endoscope 100 while observing the sheath 7 and the inside of the body using the optical imaging mechanism 103 and the ultrasonic scanning mechanism 104. After adjustment, the operator fastens the fixing screw 10 to fix the protrusion amount.

Next, on the basis of the observation result by the ultrasonic scanning mechanism 104, the stopper 11 is moved to fix the manipulation main body 9 to a desired position while considering a distance to a target tissue T on which the biopsy is performed and adjust a maximum protrusion length of the needle tube 3.

In addition, as shown in FIG. 18, a protrusion direction of the insertion body 2 from the distal end opening 107a of the channel 107 is set using the raising base 108 such that the needle tube 3 is pushed out toward the position of the target tissue T. The raising base 108 deforms the sheath 7, the needle tube 3 and the stylet 27 into a bent state by pressing the outer surface of the sheath 7. In the procedure of the biopsy with respect to the head of pancreas like the embodiment, the insertion body 2 is bent to an extent closer to a limit of performance of the bendable section 105 and the raising base 108 of the ultrasonic endoscope 100.

Next, the operator advances the needle slider 23 shown in FIG. 3 to the distal side of the manipulation section 8. Here, the operator grips both or one of the needle slider 23 and the knob 29 to maintain a state in which the knob 29 of the stylet 27 abuts the proximal end surface 25 of the positioning mechanism 24 of the proximal end of the needle slider 23 (see FIG. 13). When the operator grips the proximal portion of the needle slider 23 with her or his hands, both of the needle slider 23 and the knob 29 are easily gripped together with one hand.

In a state in which the knob 29 abuts the proximal end surface 25 of the positioning mechanism 24, the cored bar 28 of the stylet 27 withdraws the needle tip 32a of the needle tube 3 from the inner surface of the sheath 7 (see FIG. 16). For this reason, in a state in which the knob 29 abuts the proximal end surface 25 of the positioning mechanism 24, regardless of the shape into which the sheath 7 is bent by the ultrasonic endoscope 100, the needle tip 32a of the needle tube 3 cannot easily stick in the inner surface of the sheath 7.

Even when the needle tube 3 is moved in the sheath 7 to the distal side of the sheath 7 in this state, the needle tip 32a of the needle tube 3 protrudes from the distal end of the sheath 7 without sticking in the inner surface of the sheath 7 (see FIG. 18).

In this way, in the embodiment, in a state in which the distal end surface 28a of the cored bar 28 of the stylet 27 comes in contact with the inner circumferential surface 7a of the sheath 7, the needle tube 3 is advanced by the needle slider 23 toward the distal end of the sheath 7 while the cored bar 28 withdraws the needle tip 32a such that the needle tip 32a is separated from the inner circumferential surface 7a of the sheath 7.

After the needle tube 3 protrudes from the sheath 7, as shown in FIG. 18, the cored bar 28 of the stylet 27 is returned into the needle tube 3. Accordingly, the needle tube 3 can puncture the tissue with the sharp needle tip 32a of the needle tube 3. Next, in a state in which the distal end of the sheath 7 abuts the intestinal wall, as the operator further advances the needle slider 23 to the distal side of the manipulation section 8, the needle tip 32a of the needle tube 3 punctures the tissue while protruding from the distal end of the sheath 7 and is propelled into the target tissue T on which the biopsy is performed. Here, the cored bar 28 of the stylet 27 is disposed in the needle tube 3 such that the tissue that is not the biopsy target does not enter the needle tube 3.

The operator can acquire positional information of the distal side portion of the needle tube 3 inserted into the tissue using the ultrasonic scanning mechanism 104. For this reason, the operator can observe an ultrasonic wave image showing an image of the distal side portion of the needle tube 3 acquired in the ultrasonic scanning mechanism 104 using the ultrasonic observation unit 115 shown in FIG. 1. The operator causes the distal end of the needle tube 3 to arrive at the target tissue T on which the biopsy is performed with reference to the image of the distal portion of the needle tube 3 clearly projected to the ultrasonic observation unit 115.

Next, the operator pulls the stylet 27 out of the insertion body 2 and the manipulation section 8. Accordingly, a through-hole extending from the distal end of the needle tube 3 to the proximal end of the needle slider 23 is generated in the needle tube 3. The operator connects a syringe or the like to the port 26 disposed at the proximal end of the needle slider 23 to suction the inside of the needle tube 3, and suctions cells or the like of the target tissue T on which the biopsy is performed from the distal end of the needle tube 3 to collect the cells.

When a necessary amount of cells or the like is collected, the distal end of the needle tube 3 is retracted in the sheath 7 while the needle tube 3 is pulled out of the tissue as the operator retreats the needle slider 23 to the proximal side of the manipulation section 8. When the needle tube 3 is pulled out of the tissue, the operator removes the attachment adaptor 18 from the proximal port member 107b of the manipulation section 109 of the ultrasonic endoscope 100, and extracts the puncture needle 1 from the channel 107. Finally, the ultrasonic endoscope 100 is extracted from a patient to terminate a series of treatments.

As described above, in the embodiment, since the stylet 27 protruding from the distal opening section 31 of the needle tube 3 by a predetermined length separates the sharp needle tip 32a from the inner surface of the sheath 7 in the bent shape to withdraw the needle tip 32a, the needle tip 32a optimized for puncturing the tissue can protrude from the sheath 7 without sticking in the inner surface of the sheath 7. When the sheath 7 is bent close to an upper limit of the bending performance by the bendable section 105 or the raising base 108 of the ultrasonic endoscope 100, as the stylet 27 withdraws the needle tip 32a as in the embodiment, the needle tip 32a having a shape advantageous for the puncture performance with respect to the tissue can be guided to the tissue serving as the puncture target without sticking in the sheath 7.

In addition, since the positioning mechanism 24 defines the position of the distal end surface 28a with respect to the needle tube 3, the cored bar 28 of the stylet 27 cannot easily deviate with respect to the needle tube 3 in a process in which the needle tube 3 passes through the sheath 7 in the bent state.

In addition, the distal end surface 28a of the cored bar 28 with respect to the needle tip 32a of the needle tube 3 can be positioned when the knob 29 of the stylet 27 abuts the proximal end surface 25 of the positioning mechanism 24 disposed at the needle slider 23. In addition, the knob 29 may be simply pulled to the proximal side when the cored bar 28 is pulled out of the needle tube 3.

Second Embodiment

Figure 19:
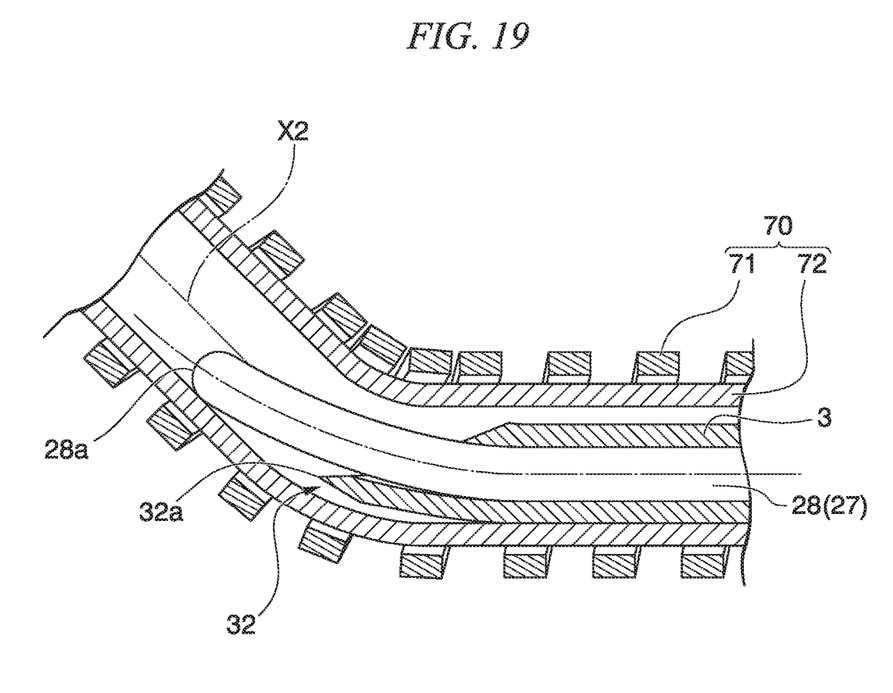
FIG. 19 is a partial cross-sectional view showing a distal portion of a puncture needle for an endoscope of a second embodiment of the present invention.

A second embodiment of the present invention will be described. FIG. 19 is a partial cross-sectional view showing a distal portion of a puncture needle for an endoscope of the second embodiment of the present invention.

A puncture needle 1A for an endoscope of the embodiment shown in FIG. 19 includes a sheath 70 having a different configuration from the sheath 7 disclosed in the first embodiment, instead of the sheath 7 disclosed in the first embodiment.

The sheath 70 has a coil body 71 and a resin tube 72.

The coil body 71 is a coil in which a metal wire is wound in a spiral shape. In the embodiment, the coil body 71 is formed by, for example, closely coiling a strand constituted by a metal wire. Further, a cross-sectional shape and a winding side of the metal of the coil body 71 are not particularly limited. The metal wire of the coil body 71 is formed in a coil shape. Physical strength applied to the sheath 70 is mainly transmitted from the proximal end to the distal end of the sheath 70 by the coil body 71 when the sheath is moved in a direction of a center line of the coil body 71 (a centerline X2 of the sheath 70) or the sheath is rotated about the center line of the coil body 71 serving as a rotational center.

The resin tube 72 is a resin tube disposed in the coil body 71 to be coaxial with the coil body 71. The resin tube 72 has an inner diameter to an extent such that the needle tube 3 can be inserted into the resin tube 72. The resin tube 72 may be fixed to the coil body 71 or may not be fixed to the coil body 71. For example, only the distal end of the resin tube 72 may be fixed to the distal end of the coil body 71.

The material of the resin tube 72 is not particularly limited. In the embodiment, like the first embodiment, since the stylet 27 is configured to prevent the needle tip 32a from sticking in the sheath 70, it is not necessary to consider whether the material of the resin tube 72 can be easily pierced by the needle tip 32a. In addition, in the embodiment, since the physical strength for advancing and retracting the insertion body 2 in the channel 107 and the physical strength for adjusting an orientation of the needle tip 32a in the channel 107 are transmitted from the manipulation section 8 through the coil body 71, the resin tube 72 may be flexible.

In the embodiment, as the sheath 70 has the coil body 71, even when the bendable section 105 of the ultrasonic endoscope 100 is bent close to the limit of the bending performance and stands close to a limit of standing performance of the raising base 108, the sheath 70 bent by the bendable section 105 or the raising base 108 can easily maintain a circular cross-sectional shape and does not easily collapse. For this reason, even when the sheath 70 is bent, a sufficient gap for enabling insertion of the needle tube 3 can be maintained in the sheath 70.

In addition, as the resin tube 72 is installed in the coil body 71, the needle tip 32a, the cored bar 28 of the stylet 27, or the like, can be prevented from entering a gap between metal strands that constitute the coil body 71. In addition, in the embodiment, the stylet 27 withdraws the needle tip 32a from the inner surface of the resin tube 72 as in the first embodiment such that the needle tip 32a does not stick in the inner surface of the resin tube 72. For this reason, a flexible tube serving as the resin tube 72 can be employed. As a result, in the embodiment, a decrease in bending performance of the bendable section 105 and the raising base 108 in a state in which the insertion body 2 is inserted into the channel 107 of the ultrasonic endoscope 100 is prevented.

While embodiments of the present invention have been described in detail above with reference to the accompanying drawings, the specific configurations are not limited to the embodiments but may include design changes or the like without departing from the spirit of the present invention. Additions, omissions, substitutions, and other variations may be made to the present invention without departing from the spirit and scope of the present invention.

In addition, the components shown in the above-mentioned embodiments may be appropriately combined.

The present invention is not limited by the above description, but by the appended claims.

What is claimed is:

1. A puncture needle that is used with an endoscope having a channel through which a medical instrument is inserted and a bending section configured to bend the medical instrument in the channel, the puncture needle being configured to be inserted through the channel as the medical instrument, the puncture needle comprising:
    a flexible sheath having a longitudinal axis and deformed to be bent by the bending section;
    a flexible needle tube having a needle tip section and an opening section formed in the needle tip section, and movable in the sheath with respect to the sheath;
    a stylet having a distal end surface that is configured to advance and retreat in the needle tube along the longitudinal axis of the sheath, and to protrude from and withdraw into the needle tube, and that is configured to be positioned with respect to the needle tube in a state in which the distal end surface protrudes from the opening section of the needle tube;
    a manipulation section attached to the sheath and configured to advance and retract the needle tube with respect to the sheath; and
    a positioning mechanism installed at the manipulation section and configured to hold the stylet with respect to the needle tube at a position at which the distal end surface of the stylet protrudes from the opening section of the needle tube,
    wherein, in a state in which the puncture needle for the endoscope is disposed in the channel, when the distal end surface of the stylet is pressed from an inner surface of the sheath bent by the bending section, a needle tip of the needle tube is moved away from an inner surface of the sheath in a state in which the distal end surface of the stylet is positioned by the positioning mechanism with respect to the needle tube.

2. The puncture needle for an endoscope according to claim 1, wherein, in a state in which a bending radius of curvature of a bent shape in the bending section which bends the sheath is a minimum value such that the needle tip does not penetrate the sheath,
    a length from the opening section of the needle tube to the distal end surface of the stylet is maintained in a positional relation in which the distal end surface of the stylet comes in contact with an inner circumferential surface of the sheath and the needle tip is spaced from the inner circumferential surface of the sheath.

3. The puncture needle for an endoscope according to claim 1, wherein the needle tube has:
    a principal inclined surface having a flat surface shape inclined with respect to a centerline of the needle tube; and
    a back-cut processed surface inclined with respect to the centerline of the needle tube and having a flat surface shape crossing the principal inclined surface to form the needle tip on an intersection line with the principal inclined surface.

4. The puncture needle for an endoscope according to claim 1, wherein the needle tube has a curved blade surface configured to form a part of a conical surface about a straight line coaxial with or parallel to the centerline of the needle tube when the needle tube is in a straight state and configuring the needle tip on a boundary line with the inner circumferential surface of the needle tube.

5. The puncture needle for an endoscope according to claim 2, wherein the sheath has:
- a coil body formed of a metal wire wound in a coil shape and having an inner diameter larger than an outer diameter of the needle tube; and
- a resin tube disposed in the coil body and coaxial with the coil body and having an inner diameter larger than the outer diameter of the needle tube.

6. A biopsy system comprising:
- an endoscope having a channel through which a medical instrument is inserted and a bending section configured to bend the medical instrument in the channel; and
- the puncture needle for an endoscope according to claim 1.

7. The biopsy system according to claim 6, wherein the bending section has at least one of:
- a bendable section configured to bend the channel, and a raising base configured to press an outer surface of the sheath to define a protrusion direction of the medical instrument from a distal end of the channel, and
- wherein a protrusion distance from an opening section of the needle tube of the puncture needle to the distal end surface of the stylet is defined based on a smaller one of a minimum value of a radius of curvature of the sheath by the bendable section and a minimum value of the radius of curvature of the sheath by the raising base, such that the needle tip does not penetrate the sheath.

* * * * *